(12) United States Patent  
Zimmermann (10) Patent No.: US 10,967,378 B2  
(45) Date of Patent: Apr. 6, 2021

(54) SAMPLE COLLECTION KIT AND METHOD FOR COLLECTING PLANT SAMPLES, IN PARTICULAR ALGAE SAMPLES

(71) Applicant: Fraunhofer-Gesellschaft zur Foerderung der angewandten Forschung e. V., Munich (DE)

(72) Inventor: Heiko Zimmermann, Waldbrunn (DE)

(73) Assignee: Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 75 days.

(21) Appl. No.: 16/310,438

(22) PCT Filed: Jun. 1, 2017

(86) PCT No.: PCT/EP2017/063334  
§ 371 (c)(1),  
(2) Date: Dec. 16, 2018

(87) PCT Pub. No.: WO2017/215939  
PCT Pub. Date: Dec. 21, 2017

(65) Prior Publication Data  
US 2019/0184399 A1 Jun. 20, 2019

(30) Foreign Application Priority Data  
Jun. 17, 2016 (EP) .................................... 16001367

(51) Int. Cl.  
*B01L 3/00* (2006.01)  
*B01L 1/00* (2006.01)  
*C12N 1/12* (2006.01)

(52) U.S. Cl.  
CPC .................. *B01L 3/545* (2013.01); *B01L 1/52* (2019.08); *C12N 1/12* (2013.01); *B01L 3/54* (2013.01);  
(Continued)

(58) Field of Classification Search  
None  
See application file for complete search history.

(56) References Cited

U.S. PATENT DOCUMENTS

| | | | |
|---|---|---|---|
| 3,648,159 A | 3/1972 | Stansell et al. | |
| 4,303,610 A * | 12/1981 | Sardisco | B01L 1/52 422/430 |

(Continued)

FOREIGN PATENT DOCUMENTS

| | | |
|---|---|---|
| CN | 201724839 U | 1/2011 |
| CN | 104401589 A | 3/2015 |

(Continued)

OTHER PUBLICATIONS

CN201724839U English translation, (Year: 2011).*

(Continued)

*Primary Examiner* — Jyoti Nagpaul  
(74) *Attorney, Agent, or Firm* — Caesar Rivise, PC (57) ABSTRACT

The invention relates to a sample collection kit (100) for collecting plant samples, in particular algae samples for biomedical applications, which sample collection kit comprises at least one sample container for holding plant samples, a plurality of sensors, by means of which sample data can be captured, a data-recording apparatus for recording the sample data, an arrangement of tools, which has collection tools designed for harvesting the plant samples and processing tools designed for processing the plant samples, an arrangement of devices, which has auxiliary devices that can be used in the collection, transport, and processing of the plant samples, a container apparatus (70), which is designed to hold the arrangement of tools and the arrangement of devices in isolation from the environment, and identification markings (80), which contain identification data and are applied to the at least one sample container (Continued)

(70) to the collection tools, and to the processing tools. The invention further relates to a sample collection method.

16 Claims, 4 Drawing Sheets

(52) U.S. Cl.
CPC ... *B01L 2200/025* (2013.01); *B01L 2200/028* (2013.01); *B01L 2200/141* (2013.01); *B01L 2300/023* (2013.01); *B01L 2300/024* (2013.01); *B01L 2300/0627* (2013.01)

(56) References Cited

U.S. PATENT DOCUMENTS 9,834,810 B2 *  12/2017  Knapp, Jr. .............. B01L 3/545
2006/0286606 A1  12/2006  Oliver

FOREIGN PATENT DOCUMENTS

DE   102005040872 B3   4/2007
WO      2009143339 A1  11/2009
WO      2011118873 A1   9/2011

OTHER PUBLICATIONS

Machine Translation for CN 201724839 U (2011).
English Abstract for DE 102005040872 B3 (2007).
International Search Report for PCT/EP2017/063334 dated Aug. 9, 2017.
English Abstract of CN 104401589 A (2015).
English Translation of Chinese Search Report dated Sep. 25, 2020.

* cited by examiner

FIG. 4

SAMPLE COLLECTION KIT AND METHOD FOR COLLECTING PLANT SAMPLES, IN PARTICULAR ALGAE SAMPLES

CROSS-REFERENCE TO RELATED APPLICATIONS

This application is a U.S. National Phase Application of PCT/EP2017/063334, filed Jun. 1, 2017, which claims priority to EP 16001367.8, filed Jun. 17, 2016, the contents of which applications are incorporated herein by reference in their entireties for all purposes.

BACKGROUND OF THE INVENTION

The invention relates to a sample collection kit which is adapted for collecting plant samples, in particular for collecting algae samples for biomedical applications. The invention further relates to a method for collecting plant samples using the sample collection kit. Applications of the invention include obtaining plant extracts, in particular for biomedical applications, e.g. obtaining alginate granulate.

Alginate is a polysaccharide which is obtained from marine algae and has numerous applications in chemical engineering, food technology and biomedicine. In biomedicine, alginate is used e.g. to produce implants. High demands in terms of the biofunctionality (in particular biocompatibility), purity and stability are placed on implants for medical applications, e.g. for use in human implant recipients. It is generally known, in order to satisfy these requirements, to subject alginates to predetermined cleaning processes in order to minimize fluctuations in the composition. It is furthermore known from DE 10 2005 040 872 B3 to document the collection location (geographic location of algae harvesting) and sample data from the collection location and from the transport of the algae to the consumer in order to minimize fluctuations in the biofunctionality of the alginates obtained from the algae.

Algae harvesting has hitherto been carried out manually by fishermen with reusable tools. The fishermen also perform initial preparation of the collected algae and, where applicable, drying. After harvesting, the collected algae are sent in a sample container, which can be provided e.g. according to DE 10 2005 040 872 B3 with sensors and a data logger, to the consumer, by whom the alginate is obtained from the dried algae, e.g. for the production of an implant.

It has, however, been shown in practice that alginates, even if their collection and transport conditions are documented, can have undesirable fluctuations in biofunctionality. The approval of plant products for medical applications are furthermore linked to strict conditions, in particular guidelines for quality assurance of the production processes and environment (e.g. GMP, "Good Manufacturing Practice") which, as a result of the previous harvesting and transport conditions, can only be satisfied with difficulty and with reduced reliability.

The stated problems not only arise in the collection of algae and the obtaining of alginate, but also in the collection of other plant samples, e.g. for the production of active ingredients.

The objective of the invention is to provide an improved sample collection kit and an improved method for collecting plant samples, in particular algae samples, with which disadvantages of conventional techniques are avoided. The sample collection kit and the method should in particular enable the obtaining of alginate with increased reliability and reproducibility of the collection and processing of algae, improved reproducibility of the composition and/or reduced fluctuations in biofunctionality. The satisfaction of standards for quality assurance, such as e.g. GMP standards, should furthermore be improved.

These objectives are solved by a sample collection kit and a method for collecting plant samples of the invention.

SUMMARY OF THE INVENTION

According to a first general aspect of the invention, the above-mentioned objective is solved by a sample collection kit which is adapted to collect plant samples, in particular algae samples, and which contains a sensor arrangement with several sensors for the detection of sample data, working equipment, for the primary collection (harvesting), transport and processing of the plant samples, e.g. to obtain a plant extract, and identification markings with identification data of the working equipment.

The sample collection kit is advantageously suitable for all phases from the collection of plant samples to the obtaining of the plant extract. All the working equipment, in particular tools and auxiliary devices, which is required up until production of the plant extract is preferably contained in the sample collection kit and at least the tools can be identified by means of the identification marking. This makes it possible to provide the plant extract together with sample data and identification data which enable full characterization of the collection and production method of the plant extract. The individual steps of the collection, transport and processing of the plant samples are furthermore standardized by the provision of working equipment so that fluctuations in the properties of the collected plant samples and the plant extract created or substances obtained from this, in particular fluctuations in biofunctionality, are reduced. If contamination or errors become apparent when using the plant samples obtained with the sample collection kit, their causes can, as a result of the complete sample data and identification data, be traced back even to the collection of the plant samples.

The sample collection kit generally represents a set of the working equipment for the collection, transport and processing of the plant samples. In detail, the sample collection kit comprises at least one sample container for receiving the plant samples. The sample container is preferably adapted for liquid-impervious receiving of plant samples and comprises e.g. a bag composed of a plastic film. The sample container advantageously offers maintenance of the moist milieu and protection against the penetration of undesirable foreign substances during transport.

The sample collection kit further comprises the sensor arrangement with several sensors, with which sample data, which represent the properties of the collected plant samples or the type of sample collection, in particular physical and/or chemical properties of the plant samples and/or physical and/or chemical conditions of the collection, transport and processing of the plant sample, can be detected, and a data-recording device (with at least one data logger) which is adapted to record the sample data. The data-recording device can comprise a data logger which is connected fixedly to the sample collection kit and one or more data loggers which are provided for connection to sample containers in the sample collection kit in order to record data during transport.

The sample collection kit advantageously comprises a tool arrangement which contains collection tools and processing tools. The collection tools are adapted for harvesting of the plant samples. Standardized collection tools are advantageously provided to the user, such as to the fisherman e.g. in the case of the collection of algae, as a result of which the conditions of the collection of the plant samples are standardized. The processing tools are adapted for processing, in particular obtaining extract, of the plant samples at a processing location which is separate from the natural collection location, in particular in a processing laboratory. The processing tools comprise the working equipment and utensils of the user of the sample collection kit which act on the plant samples during processing. As a result of the specification of the processing tools, as in the case of the collection tools, the advantage of a standardized and reproducible processing up to obtaining of the plant extract is obtained. The collection tools and the processing tools are preferably single-use working equipment which is used on a one-off basis to collect and process the plant samples of a joint batch.

The sample collection kit furthermore advantageously comprises a device arrangement with auxiliary devices which can be used in the collection, transport and processing of the plant samples and are configured in particular for a documentation of physical and/or chemical conditions during these steps.

The sample collection kit furthermore comprises a container device for receiving the collection tools, processing tools and the auxiliary devices in a state isolated from the surroundings. The container device, which preferably has a modular structure, forms a packaging of the sample collection kit. The container device advantageously provides protection of the working equipment prior to use of the sample collection kit and a defined arrangement of the working equipment, as a result of which the use of the sample collection kit is simplified e.g. by specifying a sequence of the use of collection or processing tools.

According to a second general aspect of the invention, the abovementioned objective is solved by a sample collection method for collecting plant samples in the case of which the sample collection kit according to the first general aspect of the invention is used. The sample collection method comprises the collection of plant samples at a natural sample collection location using collection tools, wherein the plant samples are transferred into the at least one sample container and sample data are recorded. The transport of the at least one sample container and the sample processing kit to a processing laboratory is subsequently carried out, wherein, during transport, the sample data are supplemented with data about the physical and/or chemical conditions of transport, in particular the transport route and the duration of transport. The production of a plant extract is subsequently carried out in the processing laboratory using the processing tools. During processing, the sample data are supplemented with information about the physical and/or chemical conditions of the processing. Finally, the finished plant extract is provided together with a data set which comprises the sample data and the identification data of the sample collection kit.

As a result of the invention, the harvesting and preparation process of plant samples, in particular of algae, is advantageously significantly improved in relation to the purity of the plant extract and the documentation and traceability of the individual method steps. The inventors have found that fluctuations in the biofunctionality of plant samples, which were obtained with conventional techniques, as a result of contaminations of the working equipment, potentially reused or inadequately cleaned tools, undefined and inadequately documented parameters of the overall process (harvesting location, harvesting time, transport time, physical and/or chemical environmental parameters, etc.) and the use of non-standardized working equipment was impaired. In contrast to the conventional techniques, the sample collection kit advantageously simplifies the production of material with reproducible properties. An important advantage of the sample collection kit recognized by the inventors furthermore lies in the fact that all the required working equipment for sample collection and processing can be accommodated in the sample collection kit and the sample collection kit can still be manually handled, in particular can be carried manually by a user. This advantage is important in particular for obtaining alginate under extreme environmental conditions e.g. on the open seas or in breakers.

The sample collection kit preferably represents a set of working equipment for complete single use of the tools and consumables. Auxiliary devices, such as e.g. documentation devices, in particular satellite receivers, clocks, communication devices, lamp and sensors can, however, be provided for single use or multiple use.

Further advantages of the invention lie in the fact that the sample collection kit represents a defined initial state for the collection of the plant samples and the use of the sample collection kit is associated with a gain in time for the user. The invention enables clear labelling of the entire sample collection kit and all of the working equipment and materials packed therein. This advantageously ensures complete traceability of all the kit components.

A further advantage of the sample collection kit lies in the increased safety for the user since he is working with standardized, new, tested tools and is optionally provided with an emergency system (communication device, first aid box) by the sample collection kit.

According to a preferred embodiment of the invention, the sample collection kit furthermore contains consumables which can be used in harvesting and processing the plant samples. The consumables comprise, for example, water, disinfectant and/or test substances, e.g. to detect foreign substances. As a result of the provision of the consumables with the sample collection kit, the reliability and reproducibility of the individual working steps are advantageously improved.

According to a further preferred embodiment of the sample collection kit, the container device is adapted to receive the collection tools and the processing tools prior to the start of the harvesting of the plant samples in a sterile state. The collection tools and the processing tools are received in a manner which is materially separated from the surroundings in the container device. The container device is preferably provided with a seal which is only intended to be destroyed at the start of the harvest.

The container device of the sample collection kit is particularly preferably constructed from several container modules which comprise a harvesting module, a documentation module and a processing module. Each container module represents a separate, sealed-off container which contains all the working equipment for the individual phases of collection and processing and/or the auxiliary devices. The harvesting module is configured to receive the collection tools. The harvesting module contains receiving elements which are adapted to the number, size and form of the required collection tools. An unintentional receiving of unsuitable collection tools is advantageously avoided. The processing module is configured to receive the processing tools. Even in the case of the processing tools, specific receiving elements are provided in the processing module, as a result of which the use of unsuitable processing tools is avoided. The documentation module preferably contains the auxiliary devices which are used, where necessary, in the collection and processing of the plant samples.

According to a further advantageous feature of the invention, the container device can be provided with a charging interface via which electrically operated auxiliary devices of the sample collection kit and optionally also electrically operated tools can be supplied with an electric charging current. Various possibilities of the electric current supply are advantageously available. For example, a wireless, inductive energy supply or a wired energy supply can be provided. The charging interface particularly preferably comprises a charging socket which is arranged for receiving the plug of a charging cable on an outer side of the container device. The sample collection kit can advantageously be electrically charged without the container device having to be opened so that the sterility of the working equipment can be maintained during charging.

The container device can furthermore be provided with a wireless or wired data interface via which an exchange of data between the data-recording device and an external control device, e.g. an external computer, is carried out.

According to a further advantageous embodiment of the invention, the collection tools can be arranged in the harvesting module and the processing tools can be arranged in the processing module next to one another so that they form a row according to the sequence of use of the respective tools in the collection and processing of the plant samples. The harvesting module and the processing module provide the tools according to the procedure of the method according to the invention as a working procedure, as a result of which the reliability and reproducibility of the use of the sample collection kit are advantageously improved.

Alternatively or additionally, the harvesting module can be provided with a release device which enables an opening of the harvesting module exclusively at a predetermined geographical sample collection location and otherwise blocks a closure of the harvesting module. The release device and its operation can be realized, for example, as described in DE 10 2005 040 872 B3.

Further advantages for use of the sample collection kit are achieved if the container modules are connected detachably to one another. To this end, the container modules are preferably provided on their outer sides with compatible connection elements, e.g. latching elements. The sample collection kit comprises, for example, a stack of assembled container modules. If the container modules have carrier grips, advantages arise for the handling of the sample collection kit and the individual container modules during the phases of collection, transport and processing of the plant samples. The container modules preferably have the same form and size so that the combinability of the container modules in order to create sample collection kits for various takes is simplified.

According to a further, particularly advantageous embodiment of the invention, the container modules have in each case a holding platform with receiving elements, e.g. a hard foam bed with receiving elements suitable for receiving the working equipment of the sample collection kit, in particular the collection and processing tools. A transport of the tools in the load-fixed state is thus advantageously enabled, the safety of the user is improved and the potential absence of a tool can be more easily recognized. Positive-locking receiving elements, the form of which is adapted to the form of the working equipment, are particularly preferably provided.

If the container device is provided with several container modules, the charging interface is preferably provided on the documentation module since this contains electrically operated auxiliary devices. Alternatively, particularly in the case of an electric connection of the container modules and/or the use of electrically operated tools and/or receiving auxiliary devices in the other modules, the charging interface can be provided on another container module.

The container device can furthermore advantageously be provided with an emergency module which contains medical aids for the user of the sample collection kit. The emergency module (first aid box) is preferably configured for coupling to the other container modules, in particular integration into the stack of container modules.

The working equipment and sensors in the sample collection kit can advantageously be selected as a function of the concrete task, particularly in the case of collection and processing of algae. The components are preferably provided with at least one of the following features. The sensors preferably comprise at least one temperature sensor, at least one moisture sensor, at least one UV sensor and/or at least one salinity sensor.

The temperature during the collection of the plant samples, during transport and optionally also during processing, can be measured with the temperature sensor. The measured temperature values are stored as sample data by the data-recording device.

The moisture sensor is preferably provided for detecting moisture in the surroundings of the collected plant samples in the sample container. Each sample container is preferably provided with a moisture sensor. The moisture data detected with the moisture sensor are also stored as sample data during collection of the plant samples and their transport with the data-recording device. The moisture sensor advantageously enables detection of damage to the sample container during transport. If the sample container is damaged, the plant samples dry out, which is apparent in the recorded moisture data.

The UV sensor is a radiation sensor, with which natural UV radiation is detected during the collection of the plant samples and their transport. The UV sensor is preferably also coupled to the sample container in order to also detect the UV exposure of the collected plant samples during transport.

The salinity sensor is adapted for detection of the salt content of the sea at the collection location and/or the collected plant samples. The salinity data stored during collection and transport enable a characterization of the plant samples and the detection of any penetration of foreign substances.

The collection tools of the sample collection kit preferably comprise at least one collection net (e.g. dip net to collect algae), at least one harvesting knife, a thickness measurement device, e.g. a sliding caliper, for detection of the thicknesses of the collected plants (e.g. the algae stalks), and sample bottles for receiving reference samples, e.g. environmental samples, such as sea water from the surroundings of the collected algae.

The processing tools comprise peeling knives, a cutting board, and protective clothing for the user of the sample collection kit, in particular during processing in the processing laboratory, such as e.g. a hood, gloves, a mouth guard and a protective coat, and/or cleaning devices, such as e.g. a cleaning brush. An intake filter for receiving dried plant components after a drying process can furthermore be provided as a processing tool.

The auxiliary devices in the sample collection kit preferably comprise a satellite receiver, a camera, a clock, and/or recording means for written documentation. Conditions of the harvesting of the plant samples, such as e.g. mussels adhering to algae, can advantageously be documented with the camera.

According to a further advantageous embodiment of the invention, at least one of the collection tools and/or the processing tools can be provided with a use indicator which is adapted to display tool use. The use indicator, in particular a water sensor, is arranged on a surface of the respective tool. In the case of a chemically operated use indicator, a chemical indicator is provided which responds e.g. to contact with water. In the event that the tool comes into contact with water, the use indicator becomes discolored so that it is apparent for the user whether the relevant tool has already been used. In the case of an electronically operated use indicator, an electronic circuit is provided which undergoes a change in state which can be read out electronically in the event of contact e.g. with water.

Detection of the performed use of tools can furthermore be used for a locking of the data-recording device. The at least one data logger can be configured for write protection which is activated as soon as a last tool was used in a specific working procedure.

Alternatively or additionally, at least one of the collection tools and/or the processing tools can have a chemical sensor which is adapted to detect substances which are foreign to the plant, e.g. animal protein in particular from microorganisms, marine animals or excrement, or inorganic compounds or environmental poisons, in the plant sample. Contaminations of the plant sample can advantageously be determined with the chemical sensor, based e.g. on a change in color.

During the sample collection method according to the invention, the plant extract obtained after the processing of the plant sample is preferably packed into an extract container which is provided with the identification data of the sample collection kit and the sample data. The combination of the plant extract and the identification and sample data is advantageously maintained during further use at the consumer, e.g. at the manufacturer of the implant.

One of the container modules of the sample collection kit is particularly preferably used to receive the extract container for transport back from the processing laboratory to the consumer. The data-recording device can also be sent together with the extract container to the consumer with the processing module.

BRIEF DESCRIPTION OF THE DRAWINGS

Further details and advantages of the invention will be described below with reference to the enclosed drawings. In the drawings.

DETAILED DESCRIPTION OF PREFERRED EMBODIMENTS

Features of preferred embodiments of the invention are described in the following with reference by way of example to a sample collection kit for the collection of algae samples for the production of alginate. The algae samples are preferably obtained from macroalgae, in particular from the algae type Laminaria. The implementation of the invention is, however, not restricted to this example, rather is correspondingly possible with other plant samples. The working equipment for the collection of algae samples which is contained in the sample collection kit is cited by way of example. The implementation of the invention is not restricted to the application of the concretely stated tools and auxiliary devices, rather can be realized with modified working equipment which is adapted to the concrete application. In particular, the container modules shown in FIGS. 2 to 4 can alternatively or additionally be provided with parts from the list provided below of working equipment. Details of the collection and processing of algae samples and the selection of suitable types of algae are not explained below in so far as they are known per se and commonplace.

The embodiment shown of sample collection kit 100 according to the invention can be modified and/or supplemented in order to improve the safety of correct use. In particular, sample collection kit 100 can be provided with an apparatus for access control, e.g. a lock which can be released wirelessly, in particular by means of a transponder or RFID chip, or activated with a key (combination lock or mechanical key), a monitoring apparatus to detect the completeness of the batch, e.g. with space sensors at individual receiving elements in the container modules, and/or a display device to display the operating state, e.g. charging state, of sample collection kit 100.

Figure 1:
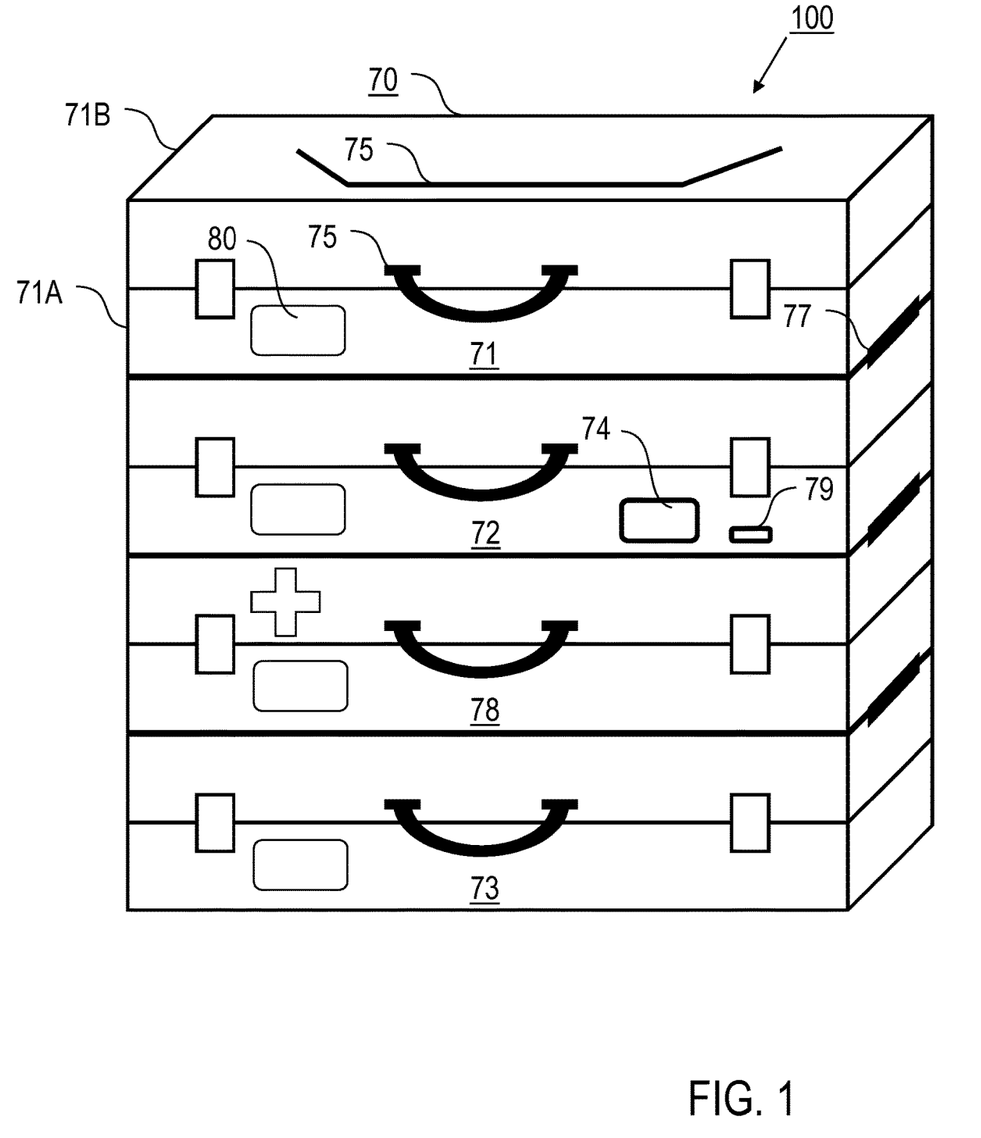
FIG. 1: shows a schematic perspective view of an embodiment of the sample collection kit according to the invention with a stack of several container modules.

FIG. 1 shows a schematic perspective view of a preferred embodiment of sample collection kit 100 according to the invention (algae kit), wherein the container device 70 thereof comprises a stack of several container modules 71, 72, 73 and an emergency module 78. Container modules 71, 72, 73 are, in the closed state, coupled via connection elements 77 which are complementary to one another and which are arranged on the outer sides of container modules 71, 72, 73. The container modules comprise a harvesting module 71 (see FIG. 2), a documentation module 72 (see FIG. 3) and a processing module 73 (see FIG. 4). Container modules 71, 72, 73 are labelled graphically and/or textually (e.g. 71: "SEA", 72: "DOC", 73: "LAB", 78: "SOS") in accordance with their function and equipment.

Each of container modules 71, 72, 73 is a case (trunk), e.g. composed of plastic and/or metal, with a base part 71A and a cover part 71B which are connected to one another via hinges. In the closed state, container modules 71, 72, 73 are closed on all sides so that their inner space is materially separated from the surroundings and can be provided in a sterile state up until first opening. Carrier grips 75 on end sides and/or cover parts 71B are adapted for manual transport of container modules 71, 72, 73 individually or in combination.

Identification markings 80 on the outer sides of container modules 71, 72, 73 comprise water-resistant markings, e.g. bar codes, QR codes, wirelessly readable memories, in particular transponders, and/or sequences of characters composed of numbers and/or letters which contain identification data of sample collection kit 100. The working equipment which is brought together in sample collection kit 100 and can be removed from the container modules is provided with identification markings 80 of the same or a modified type which contain the same identification data of sample collection kit 100.

Documentation module 72 is, on its outer surface of the respective base part, provided with a charging interface 74 in the form of a charging socket (e.g. cold-device plug socket) via which electrically operated auxiliary devices (e.g. satellite receivers, mobile telephone) in documentation module 72 can be supplied with electric charging current via an internal charging device. It is thus ensured that all the devices can be made ready for operation at harvesting without damaging the seal of sample collection kit 100. A data interface 79 via which data from an internal data-recording device can be read is furthermore provided on documentation module 72.

Figure 2:
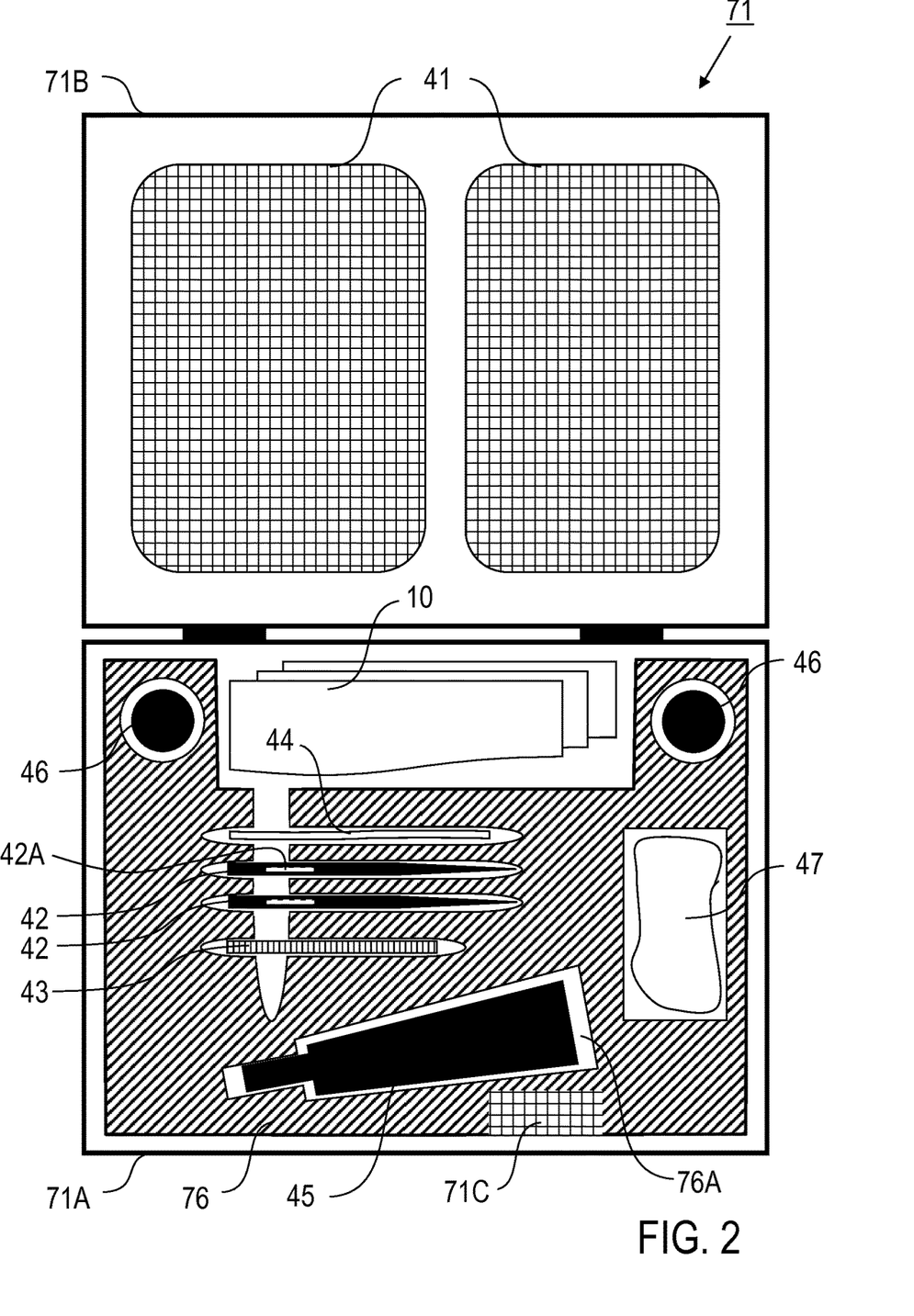
FIG. 2: shows a schematic illustration of the content of a harvesting module of the sample collection kit.

FIG. 2 shows the harvesting module 71 of sample collection kit 100 schematically in the opened state with a top view onto base part 71A and cover part 71B. A holding platform 76 with receiving elements 76A for collection tools 41, 42, . . . , which are used to harvest algae samples is provided in base part 71A for sample containers 10. Holding platform 76 is an adapted positive-locking hard foam bed in which receiving elements 76A are formed as recesses with the outer form of the individual components. Harvesting module 71 furthermore contains a schematically shown release device 71C which is coupled to a satellite receiver and blocks a closure of harvesting module 71 until harvesting module 71 is located at a predetermined geographic sample collection location.

The collection tools in base part 71A comprise two harvesting knives 42, a thickness measuring device 43, marking elements 44, a rinsing or spray bottle 45, two sample bottles 46 and film material 47. Harvesting knives 42 are, for example, shown with use indicators 42A which have e.g. a change in color in the case of contact of harvesting knives 42 with water. Harvesting knives 42 can furthermore be provided with chemical sensors in order to detect foreign substances. Thickness measurement device 43 is a ruler or a slide rule with which the thickness of the harvested algae samples is measured. The measured thicknesses are captured with the recording means for written documentation in documentation module 72. Marking elements 44 are bands which bear in each case an identification marking with the identification data of sample collection kit 100 and are provided for fixing on sample containers 10. Marking elements 44 can advantageously simultaneously be provided for a closure of sample containers 10. Rinsing bottle 45 contains salt-free or saline water for rinsing the harvested algae samples prior to these being received in one of sample containers 10. Using sample bottles 46, environmental samples, e.g. water samples, can be taken at the harvesting location and transported jointly with the harvested algae samples to the processing laboratory. Film material 47 is provided as an auxiliary material, e.g. for packaging purposes. The collection tools in cover part 71B comprise two collection nets 41 for harvesting the algae samples from the sea water.

Figure 3:
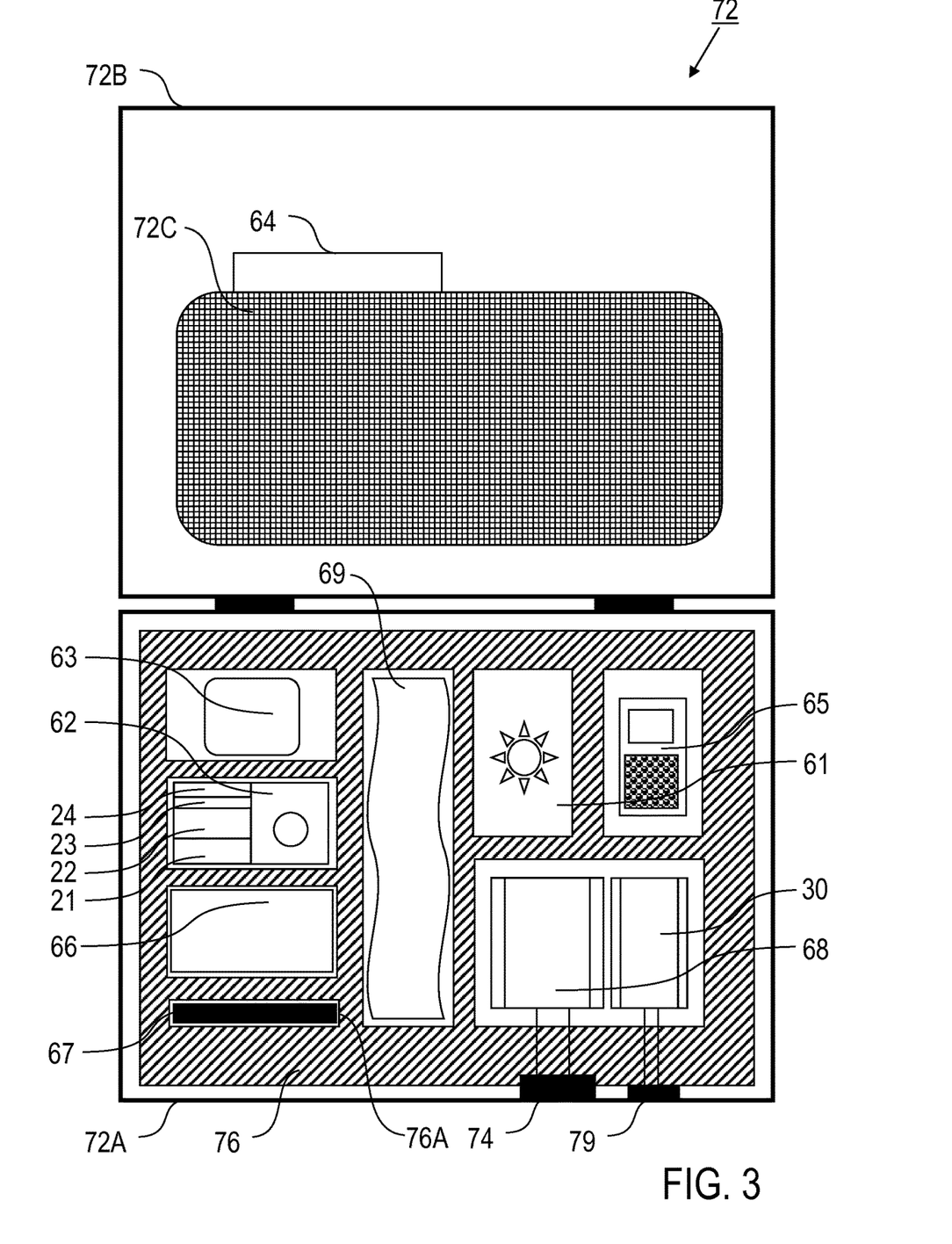
FIG. 3: shows a schematic illustration of the content of a documentation module of the sample collection kit.

Documentation module 72 shown schematically in the opened state in FIG. 3 has, in base part 72A, a holding platform 76 with receiving elements 76A for auxiliary devices 61, 62, . . . , in particular for documentation purposes, and, in cover part 72B, a compartment 72C for recording means 64 for written documentation, e.g. a writing pad.

The auxiliary devices in base part 71A comprise at least one satellite receiver 61, a camera 62, a clock 63, a mobile telephone 65, printed operating instructions 66, a writing device 67, a charging device 68 and protective clothing 69 for the user of sample collection kit 100. Charging device 68 is on one hand connected to charging interface 74 and on the other hand can be coupled to the electrically operated auxiliary devices with electric accumulators via charging cables (not represented). Protective clothing 69 comprises, for example, a hood or a hair net, mouth protection and gloves for the user during processing of the algae samples and the production of alginate granulate.

A sensor arrangement with several schematically shown sensors 21, 22, . . . and a data-recording device 30 (data logger) for recording sample data are furthermore arranged in base part 71A. Data-recording device 30 is connected to data interface 79. Further data loggers (not shown) are provided for connection to sensors and for insertion into sample containers 10 with algae samples after harvesting during transport to the processing laboratory.

Sensors 21, 22, . . . comprise e.g. moisture sensors 21 for moisture measurement in sample containers 10 after harvesting and during transport, a temperature sensor 22 for air and/or water temperature measurement during use of sample collection kit 100, UV sensors 23 for UV radiation measurement at sample containers 10 after harvesting and during transport and/or a salinity sensor 24.

In modified embodiments of the invention, other or further auxiliary devices can be contained in documentation module 72 or other container modules. For example, data-recording device 30 can be replaced by a computer, and/or components 61, 62, 63 and 65 and data-recording device 30 can be integrated in a common device, such as a microcomputer or a smart phone. Alternatively or additionally, further sensors can be provided for capturing weather data, the chlorophyll concentration of the algae samples or morphological data of the algae samples. Moreover, several satellite receivers 61 can be provided which are arranged in sample containers 10 during transport of the algae samples.

Figure 4:
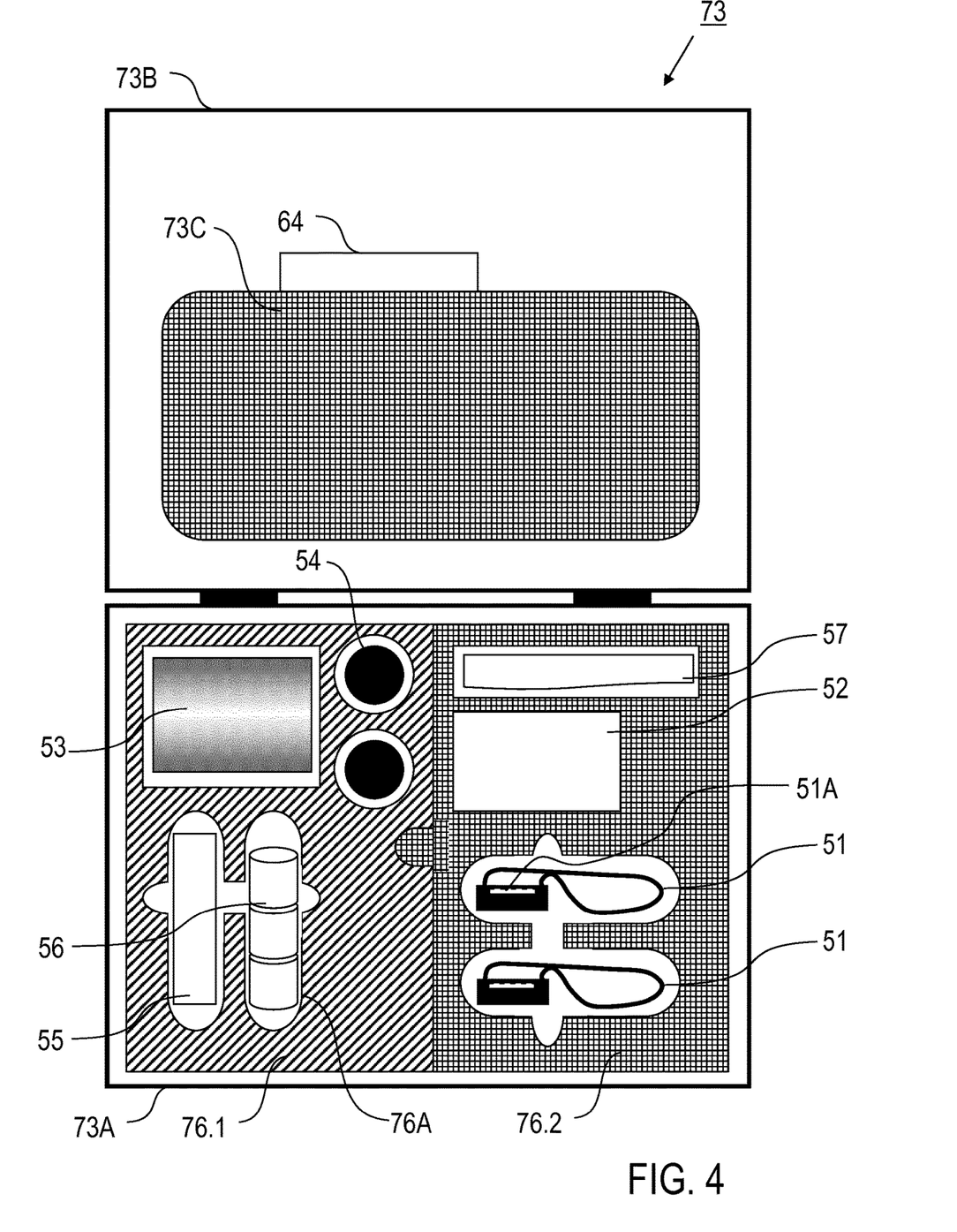
FIG. 4: shows a schematic illustration of the content of the processing module of the sample collection kit.

According to FIG. 4, processing module 73 comprises, in base part 73A, two holding platforms 76.1, 76.2 with receiving elements 76A for processing tools 51, 52, . . . and optionally further auxiliary devices and, in cover part 73B, a compartment 73C for further recording means 64 for written documentation or written operating instructions. Retaining platforms 76.1, 76.2 form two partially overlapping planes with different processing tools 51, 52, . . . .

The processing tools comprise e.g. two peeling knives and/or cleavers 51, a cutting board 52, filter material 53, reservoir container 54 for treatment liquids, in particular disinfectants, a cleaning device 55, in particular a brush, and extract containers 56, 57, such as e.g. cans 56 and bags 57. Peeling knives and/or cleavers 51 are shown by way of example with chemical sensors 51A for the detection of foreign substances, which have e.g. a change in color in the presence of animal protein in the plant samples. Peeling knives and/or cleavers 51 can furthermore be provided with use indicators.

In one concrete exemplary embodiment, sample collection kit 100 has a content according to the following list of working equipment:

1 printed operating instructions 66,
   6 labels with identification markings 80,
   5 address labels for dispatch to the consumer,
   8 UV-resistant plastic bags as sample container 10,
   9 marking elements 44 in each case with a bar code which contains the identification data,
   1 thermometer (min-max),
   19 pairs of single-use gloves,
   1 spray bottle 45 (volume 1 l),
   1 g disinfectant, e.g. Micropur,
   1 rubbish bag,
   3 closable test sample tubes 46 (50 ml),
   1 collection net 41 (with carabiner hooks),
   1 harvesting knife 42,
   1 cleaver (length of blade 15 cm), 1 reference model for determination of size,
1 satellite receiver 61,
1 mobile telephone,
2 data loggers,
1 digital camera,
1 clock with alarm/wakeup function,
1 clipboard of A5 format as a writing pad,
1 writing device 67,
4 laboratory coats of various sizes,
8 hair nets,
8 face masks,
1 hand brush 55,
1 cutting board 52 (30 cm×22 cm),
2 peeling knives 51,
12 extract bags 57 of various sizes,
1 filter 53, and
1 minute book 64.

The collection and processing of algae samples to obtain alginate extract comprise e.g. the following steps.

Sample collection kit 100 is loaded prior to the harvesting phase at the coast or on the open seas. During harvesting, continuous time measurement in the process (clock), ongoing disinfection (e.g. with Micropur), ongoing handwritten documentation (clipboard, writing device, minute book) take place. After preparation of solutions with tap water, starting of the data loggers, actual harvesting (fishing out the algae, use of harvesting knife and net), cutting of the algae and size measurement (measuring device, thickness measuring device) are carried out. Disinfection of the algae samples (e.g. with Micropur) and packaging of the algae samples in light-protected sample containers 10 (bags, closed with marking elements 44 and provided with data loggers, satellite receivers) subsequently follow. Water samples are additionally taken in sample bottles 46.

After transport onto land and to the processing laboratory, preparation (processing) is carried out in the laboratory. To this end, protective clothing 69 contained in sample collection kit 100 is first put on (gloves, coat, hair net, mouth protection). All of the data loggers are read out from the sample containers. The algae samples are subsequently cleaned, wherein hand brush 55 and a micro cutter blade are used. A cutting and a peeling of the algae, taking of a water sample with tap water and fine cutting of the algae to form algae granulate are carried out, which algae granulate undergoes, where applicable, a precipitation step to obtain the alginate.

The algae granulate or alginate is dried in a drying cabinet of the processing laboratory and removed from the drying cabinet with a suction apparatus and filter 53. The dried algae granulate is packed under vacuum in extract containers 56, 57. Extract containers 56, 57 are provided with a unique code of the sample collection kit 100 (e.g. label with bar code) and sent together with a thermometer (min-max) to the consumer.

The features of the invention disclosed in the above description, the drawings and the claims can be of significance both individually and in combination or in sub-combination in order to achieve the invention in its various configurations.

The invention claimed is:

1. A sample collection kit which is configured for collecting plant samples, comprising:
   at least one sample container which is configured for receiving plant samples,
   a sensor arrangement with several sensors with which sample data can be captured,
   a data-recording device which is configured for recording sample data,
   a tool arrangement with collection tools which are configured for harvesting of the plant samples, and with processing tools which are configured for processing of the plant samples,
   a device arrangement with auxiliary devices which can be used in collecting, transporting and processing of the plant samples,
   a container device which is configured to receive the tool arrangement and the device arrangement in a state isolated from surroundings thereof, wherein the container device is provided with a charging interface via which electrically operated auxillary devices of the device arrangement can be supplied with electric charging current, and
   identification markings which contain identification data and are applied to the at least one sample container, the collection tools and the processing tools.

2. The sample collection kit according to claim 1, further comprising
   consumables which can be used in the harvesting and processing of the plant samples.

3. The sample collection kit according to claim 1, wherein the container device is configured to preserve a sterile state of the collection tools and the processing tools before harvesting of the plant samples starts.

4. The sample collection kit according to claim 1, wherein the container device has several container modules which comprise a harvesting module which contains the collection tools, a documentation module which contains the auxiliary devices, and a processing module which contains the processing tools.

5. The sample collection kit according to claim 4, wherein the container modules have at least one of the features:
   the collection tools and the processing tools are arranged in each case in rows next to one another in the harvesting module and in the processing module, wherein the rows correspond to a predetermined sequence of the use of the collection tools and the processing tools in the collection and processing of the plant samples,
   the harvesting module is provided with a release apparatus which enables an opening of the harvesting module exclusively at a predetermined geographical sample collection location,
   the container modules are connected detachably to one another,
   the container modules have carrier grips for manual transport of the container modules,
   the container modules have the same form and size,
   the container modules have in each case at least one holding platform with receiving elements for receiving parts of the sample collection kit, and
   the container modules have on their outer sides mutually compatible connection elements.

6. The sample collection kit according to claim 4, wherein the container device has an emergency module which contains medical aid for use by users of the sample collection kit.

7. The sample collection kit according to claim 1, wherein the charging interface comprises a charging socket which is arranged on an outer side of the container device.

8. The sample collection kit according to claim 1, which has at least one of the features
   the sensors comprise at least one of at least one temperature sensor, at least one moisture sensor, at least one UV sensor and at least one salinity sensor, the collection tools comprise at least one of at least one collection net, at least one harvesting knife, a thickness measurement device, marking elements, a flushing bottle and at least one sample bottle, the processing tools comprise at least one peeling knife, at least one of at least one cleaver, a cutting block, filter material, a reservoir container, a cleaning device and a transport container, and the auxiliary devices comprise at least one of a satellite receiver, a camera, a clock, a mobile telephone, printed operating instructions, a writing device, a charging device, recording means for written documentation and protective clothing for the user of the sample collection kit.

9. The sample collection kit according to claim 1, comprising at least one of the features at least one of the collection tools and the processing tools has a use indicator which is configured to display tool use, and at least one of the collection tools and the processing tools has a chemical sensor which is configured to detect foreign substances in the plant sample.

10. A sample collection method for collecting plant samples, wherein the sample collection kit according to claim 1 is used, comprising the steps:

(a) collecting the plant samples at a natural sample collection location, wherein the collection tools are used, the collected plant samples are received in the at least one sample container and the sample data are recorded in the data-recording device, (b) transport of the at least one sample container and the sample collection kit to a processing laboratory, wherein the sample data are supplemented in the data-recording device, (c) producing a plant extract in the processing laboratory, wherein the processing tools are used and the sample data are further supplemented in the data-recording device, and (d) providing the plant extract and a data set, comprising the sample data and the identification data, for further use of the plant extract.

11. The sample collection method according to claim 10, wherein the sample data comprise information about the collection location, a temperature during collection, transport and processing, and a transport route.

12. The sample collection method according to claim 10, wherein step (a) further comprises collecting environmental samples from the sample collection location.

13. The sample collection method according to claim 10, comprising at least one of the features in step (d), the plant extract is packed in an extract container which is provided with the identification data of the sample collection kit and the sample data, and in step (d), the extract container with the plant extract is arranged in the container device and is provided for further transport to a consumer.

14. The sample collection method according to claim 10, wherein the plant samples comprise algae.

15. The sample collection method according to claim 14, in which the plant samples comprise algae for biomedical applications.

16. The sample collection kit according to claim 1, wherein the sample collection kit is configured for collecting algae samples for biomedical applications.

* * * * *